(12) United States Patent
Schaffer

(10) Patent No.: US 9,554,732 B2
(45) Date of Patent: Jan. 31, 2017

(54) MODULAR PHYSICAL ACTIVITY MONITORING SYSTEM

(71) Applicant: Jonathan C. Schaffer, Burlingame, CA (US)

(72) Inventor: Jonathan C. Schaffer, Burlingame, CA (US)

(73) Assignee: EVERYDAY OLYMPIAN, INC., Burlingame, CA (US)

( * ) Notice: Subject to any disclaimer, the term of this patent is extended or adjusted under 35 U.S.C. 154(b) by 0 days.

(21) Appl. No.: 14/746,626

(22) Filed: Jun. 22, 2015

(65) Prior Publication Data

US 2015/0375042 A1 Dec. 31, 2015

Related U.S. Application Data

(60) Provisional application No. 62/018,678, filed on Jun. 30, 2014.

(51) Int. Cl.
*A63B 24/00* (2006.01)
*A61B 5/11* (2006.01)
*A61B 5/00* (2006.01)

(52) U.S. Cl.
CPC ............ *A61B 5/1118* (2013.01); *A61B 5/1116* (2013.01); *A61B 5/6804* (2013.01); *A61B 5/1123* (2013.01); *A61B 5/6806* (2013.01); *A61B 5/6807* (2013.01); *A61B 5/7275* (2013.01); *A61B 2505/09* (2013.01)

(58) Field of Classification Search
CPC ..... A63B 24/00; A63B 24/0062; A63B 71/06; A63B 59/20; A63B 69/3608; G06F 17/40; A61B 5/1118; A61B 5/1116; A61B 5/1123; A61B 5/6804; A61B 5/6806; A61B 5/6807; A61B 5/7275; A61B 2505/09
See application file for complete search history.

(56) References Cited

U.S. PATENT DOCUMENTS

| | | | |
|---|---|---|---|
| 6,428,490 B1 | 8/2002 | Kramer et al. | |
| 6,913,559 B2 | 7/2005 | Smith | |
| 7,008,231 B2 * | 3/2006 | Pesnell | A63B 59/20 |
| | | | 345/156 |
| 7,780,541 B2 * | 8/2010 | Bauer | A61B 5/225 |
| | | | 2/161.2 |
| 8,162,857 B2 | 4/2012 | Lanfermann et al. | |
| 8,221,291 B1 | 7/2012 | Kantarevic | |
| 8,572,764 B2 | 11/2013 | Thellmann | |
| 9,043,004 B2 * | 5/2015 | Casillas | G01L 1/205 |
| | | | 700/91 |
| 9,259,613 B2 * | 2/2016 | Case, Jr. | G06F 17/40 |
| 9,414,784 B1 * | 8/2016 | Berme | A61B 5/1122 |
| 2006/0211523 A1 * | 9/2006 | Sabatino | A63B 69/3608 |
| | | | 473/453 |
| 2013/0192071 A1 | 8/2013 | Esposito et al. | |

(Continued)

*Primary Examiner* — Glenn Richman
(74) *Attorney, Agent, or Firm* — Foley & Lardner LLP

(57) ABSTRACT

A system includes an activity-specific article and an activity-agnostic puck. The article includes a receptacle and an activity-specific sensor coupled to the receptacle. The puck is configured to be removably positioned in the receptacle. The puck includes a processor, a communication interface, and at least one activity-agnostic sensor coupled to the processor. The processor receives information from the activity-specific sensor and the activity-agnostic sensor, and provides the received information through the communication interface.

17 Claims, 13 Drawing Sheets

(56) References Cited

U.S. PATENT DOCUMENTS

| | | | |
|---|---|---|---|
| 2014/0031703 A1 | 1/2014 | Rayner et al. | |
| 2014/0172134 A1* | 6/2014 | Meschter | G01L 1/205 700/91 |
| 2015/0182842 A1* | 7/2015 | Martikka | A63B 71/06 340/870.07 |
| 2015/0290495 A1* | 10/2015 | Woo | A61B 5/0002 700/91 |

* cited by examiner

MODULAR PHYSICAL ACTIVITY MONITORING SYSTEM

CROSS-REFERENCE TO RELATED PATENT APPLICATIONS

This application claims the benefit of U.S. Provisional Patent Application 62/018,678 filed Jun. 30, 2014 to Jonathan Schaffer, titled "MODULAR PHYSICAL ACTIVITY MONITORING SYSTEM," the contents of which are incorporated herein by reference in their entirety.

BACKGROUND

Field of the Disclosure

The present disclosure relates generally to systems and methods for measuring, collecting, storing, communicating, permissioning, processing, analyzing and displaying data acquired by sensor components distributed on, around or within the body.

SUMMARY

In an aspect, a system includes an activity-specific article and an activity-agnostic puck. The article includes at least one receptacle and at least one activity-specific sensor coupled to the receptacle. The puck is configured to be removably positioned in the receptacle. The puck includes a processor, a communication interface, and at least one activity-agnostic sensor coupled to the processor. The processor receives information from the activity-specific sensor and the activity-agnostic sensor, and provides the received information through the communication interface.

In another aspect, a method includes, while a puck is removably positioned in a first receptacle, collecting first activity-specific sensor information through the first receptacle during a first activity period; and transmitting second activity information from a memory of the puck through a communication interface of the puck. The second activity information represents second activity-specific sensor information received by the puck through a second receptacle during a second activity period prior to the first activity period, and further represents activity-agnostic sensor information received from within the puck during the second activity period In another aspect, a sealed removable puck includes a processor, a communication interface coupled to the processor, a sensor, a sensor interface coupled to the sensor, and a physical interface. The processor identifies, through information received via the physical interface when coupled to the receptacle, an activity-specific article to which the receptacle is attached. The processor receives activity-specific sensor information through the physical interface and activity-agnostic sensor information from the sensor interface. The processor provides the received activity-specific and activity-agnostic sensor information wirelessly through the communication interface.

BRIEF DESCRIPTION OF THE DRAWINGS

Advantages and features of the present disclosure will become better understood with reference to the following more detailed description and claims taken in conjunction with the accompanying drawings, in which like elements are identified with like symbols.

DETAILED DESCRIPTION

There is a growing demand in consumer, industrial and clinical environments for systems and devices to measure, record, analyze and share greater amounts of physiological and biomechanical information. The applications for such systems and devices are wide ranging and include, but are not limited to, the automatic capture and identification of strength, resistance, kinesthetic and cardio training data, the permissioned sharing of health and fitness data with third party professionals, the reduction of injury and waste through the wide-scale and unobtrusive measurement of worker time and motion data, and the automatic recognition of symptoms indicative of serious health problems when they arise, as opposed to retrospectively at regularly scheduled appointments.

The present disclosure relates generally to systems and methods for measuring, collecting, storing, communicating, permissioning, processing, analyzing and displaying data acquired by sensor components distributed on, around or within the body.

Measurements may be taken from one or more sensors. In one or more embodiments, sensors detect forces applied to a body, or forces applied by a body. In one or more embodiments, sensors detect position, motion, and rates of change of motion.

Sensors may be associated with or incorporated into garments, apparel, accessories or gear. Sensors may include flexible and stretchable fabric-based force measuring sensors.

Uniquely identifiable, interchangeable and assignable sensor sub-systems allow for quick coupling, decoupling and recoupling of activity-agnostic system components and activity-specific system components. Sensors and sensor systems provide real-time, near real-time, and batch processed feedback relating to current or historical body conditions, forces and motion. This feedback allows for the provision of notifications, alerts, trends and anomaly detection, both to users and to permissioned third party professionals.

Figure 1:
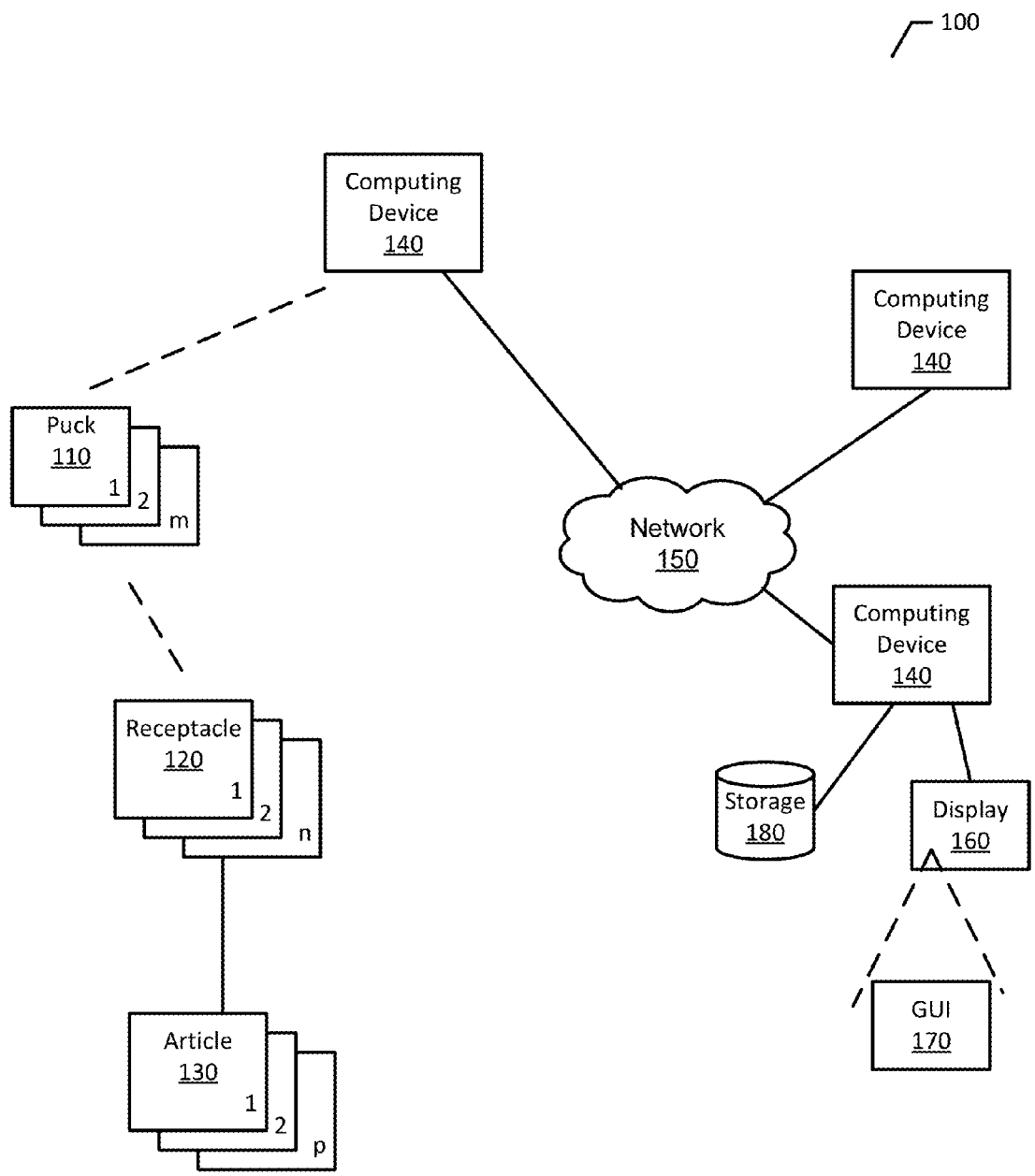
FIG. 1 is an illustration of a physical activity monitoring system according to an embodiment of the present disclosure.

FIG. 1 illustrates a modular physical activity monitoring system 100 according to an embodiment of the present disclosure. System 100 includes one or more pucks 110 and one or more receptacles 120 for receiving the pucks 110. One or more of receptacles 120 are attached to each of one or more articles 130. Pucks 110 communicate with a computing device 140, and information provided by a puck 110 may be provided through a network 150 to one or more other computing devices 140. As illustrated in FIG. 1 for one computing device 140, but may be generally applicable, computing device 140 may include a display 160 with a graphical user interface 170, and may further include storage 180.

By way of an example in overview, during a physical activity monitoring session, a subject may wear multiple articles 130, each of which includes one (or more) receptacle 120. Each receptacle 120 may have a puck 110 placed therein; however, it is not necessary that each receptacle 120 of article 130 includes a puck 110. Information related to data received from sensors (described below) is stored in puck 110, and/or is provided to a local external computing device 140. In one or more embodiments, information is provided through GUI 170 on display 160 of the local computing device 140. The information may alternatively or additionally be sent through network 150 to another computing device 140, such as a device of a third party professional (e.g., a physical trainer or physician). A detailed description of components of system 100 follows.

Puck 110 is small and lightweight so as to minimize interference with a subject's physical activity. In one or more embodiments, puck 110 is humidity and water resistant, or is waterproof, to allow, for example, physical activity in the rain or in a pool, or to minimize risk of damage if puck 110 is inadvertently laundered. Puck 110 is readily placed in, and readily removed from, receptacle 120. Puck 110 is not specific to any one receptacle 120, and is configured generically, to be interchangeably placed in multiple ones of the receptacles 120 at different times. Accordingly, puck 110 is agnostic as to any given receptacle 120. Further details of puck 110 are provided below.

Receptacle 120 is specific to a particular intended positioning on an article 130. By way of example, in one or more embodiments, an article 130 is a full bodysuit that may include twenty-one (or more, or less) receptacles 120 (e.g., one at the head, one at the upper torso, one at the lower torso, and one at each of the shoulders, elbows, wrists, hands, hips thighs, knees, ankles, and feet). Each of the receptacles 120 is specific to the corresponding body portion that it is positioned to monitor. In such a full bodysuit, one or more pucks 110 may be placed in receptacles 120 according to a particular physical activity to be performed. Receptacles 120 include sensors for monitoring specific activities at the associated body portion. Further details of receptacle 120 are provided below.

Article 130 is positioned on the body to monitor a portion or portions of the body. In the example of the full bodysuit, one article 130 provides for monitoring of many portions of the body. In other embodiments, article 130 provides for monitoring fewer portions of the body. For example, article 130 may be a glove, a sock, a neck scarf, a knee brace, an elbow pad, or a shoe. Further details of article 130 are provided below.

Computing device 140 is a workstation, telephone, desktop computer, laptop or notebook computer, tablet computer, server, mobile telephone (e.g., smart phone), personal digital assistant, media playing device, gaming system, mobile computing device, wearable computing device, or any other type and/or form of computing, telecommunications or media device that is capable of communication, and that has sufficient processor power and memory capacity to perform the operations described herein. In one or more embodiments, the computing device 140 may have different processors, operating systems, and input devices. Further details of computing device 140 are provided below.

Network 150 represents any type of network, such as a wide area network or a local area network, mesh network, or a combination of networks. Network 150 may include one or more of analog and digital networks, wide area and local area networks, wired and wireless networks, and broadband and narrowband networks. In some implementations, network 150 may include a cable (e.g., coaxial metal cable), satellite, fiber optic, or other wired connection.

Display 160 may be part of computing device 140, or may be separate from computing device 140. For example, with respect to a server, display 160 may be physically separate (e.g., in another room) from computing device 140; whereas, for a mobile phone, display 160 is integrated into computing device 140.

GUI 170 provides an interface between computing device 140 and a person viewing display 160. In one or more embodiments, in addition to the graphical portion of GUI 170, there is an audio portion of GUI 170, such as for verbal interaction between the person and computing device 140. In one or more embodiments, in addition to the graphical and audio portion of GUI 170, there is a haptic portion of GUI 170, such as for physical feedback to the person from computing device 140.

Storage 180 is information storage external to computing device 140, providing additional storage space for the potentially large amount of data that may be accumulated from pucks 110 of one or more subjects.

Details of certain components of modular physical activity monitoring system 100 are provided next.

As noted above, there may be one or more computing devices 140 in modular physical activity monitoring system 100. Additionally, puck 110 may include a computing device.

Figure 2:
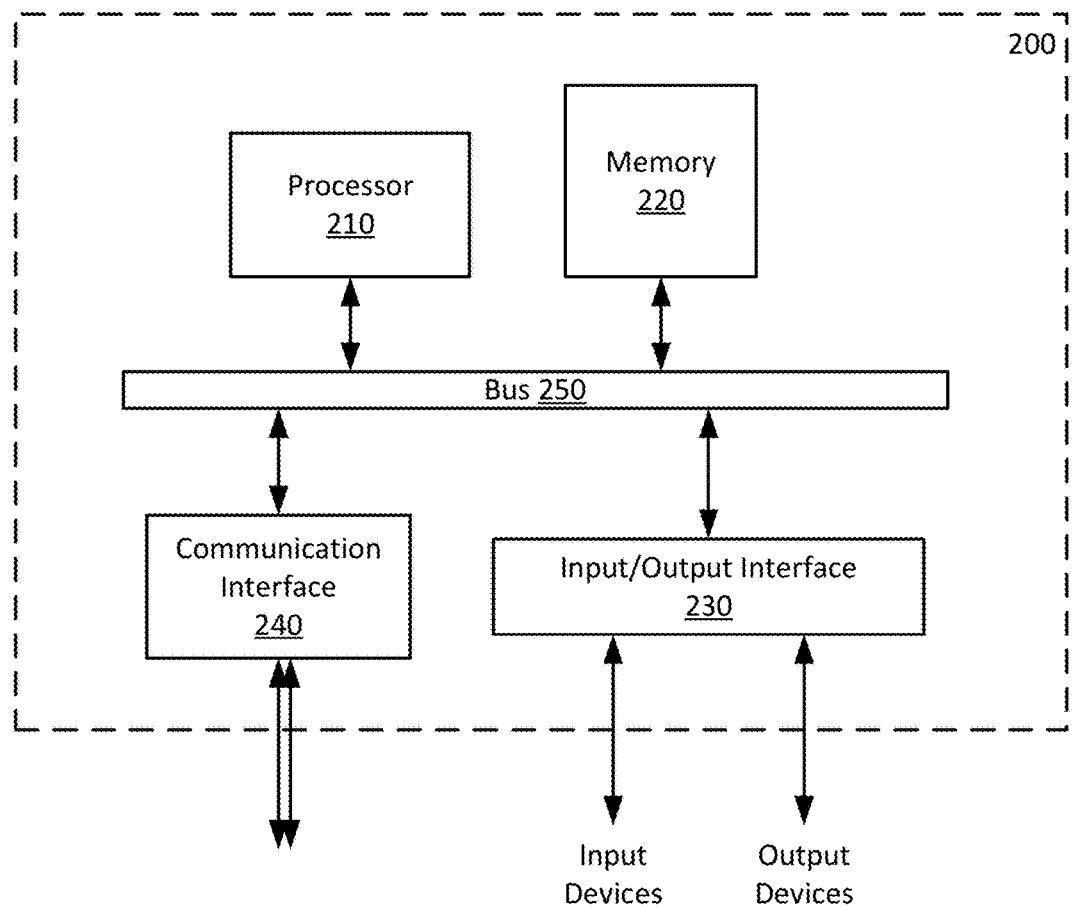
FIG. 2 is a block diagram of an example of a computing device according to an embodiment of the present disclosure.

FIG. 2 illustrates an example of a computing device 200 (e.g., computing device 140) that includes a processor 210, a memory 220, an input/output interface 230, and a communication interface 240. A bus 250 provides a communication path between two or more of the components of computing device 200. The components shown are provided by way of illustration and are not limiting. Computing device 200 may have additional or fewer components, or multiple of the same component.

Processor 210 represents one or more of a general-purpose processor, digital signal processor, microprocessor, microcontroller, application specific integrated circuit (ASIC), field programmable gate array (FPGA), other circuitry effecting processor functionality, or a combination thereof, along with associated logic and interface circuitry.

Memory 220 represents one or both of volatile and non-volatile memory for storing information (e.g., instructions and data). Examples of memory include semiconductor memory devices such as EPROM, EEPROM, flash memory, RAM, or ROM devices, magnetic media such as internal hard disks or removable disks or magnetic tape, magneto-optical disks, CD-ROM and DVD-ROM disks, holographic disks, and the like.

Portions of modular physical activity monitoring system 100 may be implemented as computer-readable instructions in memory 220 of computing device 200, executed by processor 210.

Input/output interface 230 represents electrical components and optional code that together provide an interface from the internal components of computing device 200 to external components. Examples include a driver integrated circuit with associated programming, or an interface to storage 180.

Communication interface 240 represents electrical components and optional code that together provides an interface from the internal components of computing device 200 to external networks, such as network 150. Communication interface 240 may be bi-directional, such that, for example, data may be sent from computing device 200, and instructions and updates may be received by computing device 200.

Bus 250 represents one or more interfaces between components within computing device 200. For example, bus 250 may include a dedicated connection between processor 210 and memory 220 as well as a shared connection between processor 210 and multiple other components of computing device 200.

An embodiment of the disclosure relates to a non-transitory computer-readable storage medium (e.g., a memory 220) having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the embodiments of the disclosure, or they may be of the kind well known and available to those having skill in the computer software arts.

Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel. Another embodiment of the disclosure may be implemented in hardwired circuitry in place of, or in combination with, machine-executable software instructions.

Figure 3A:
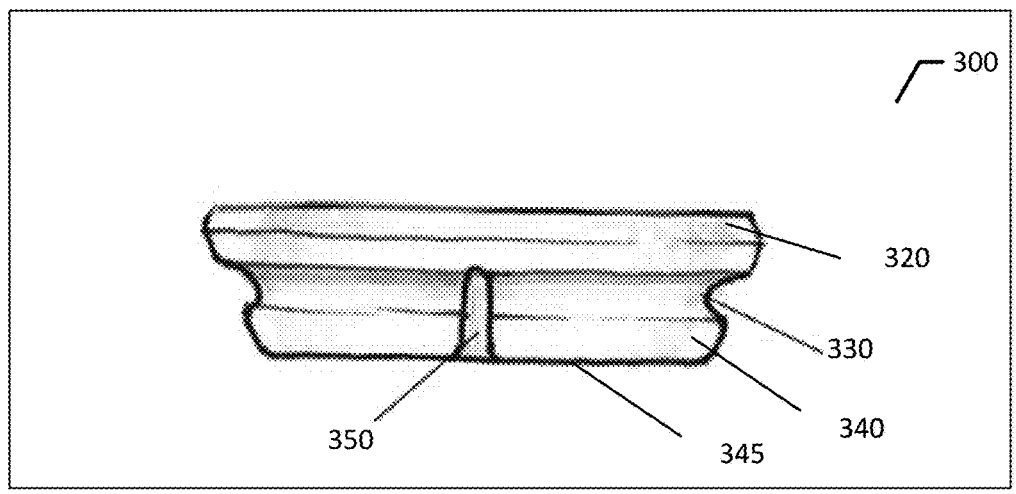
FIG. 3A is a side view illustration of an example of a puck according to an embodiment of the present disclosure.
Figure 3B:
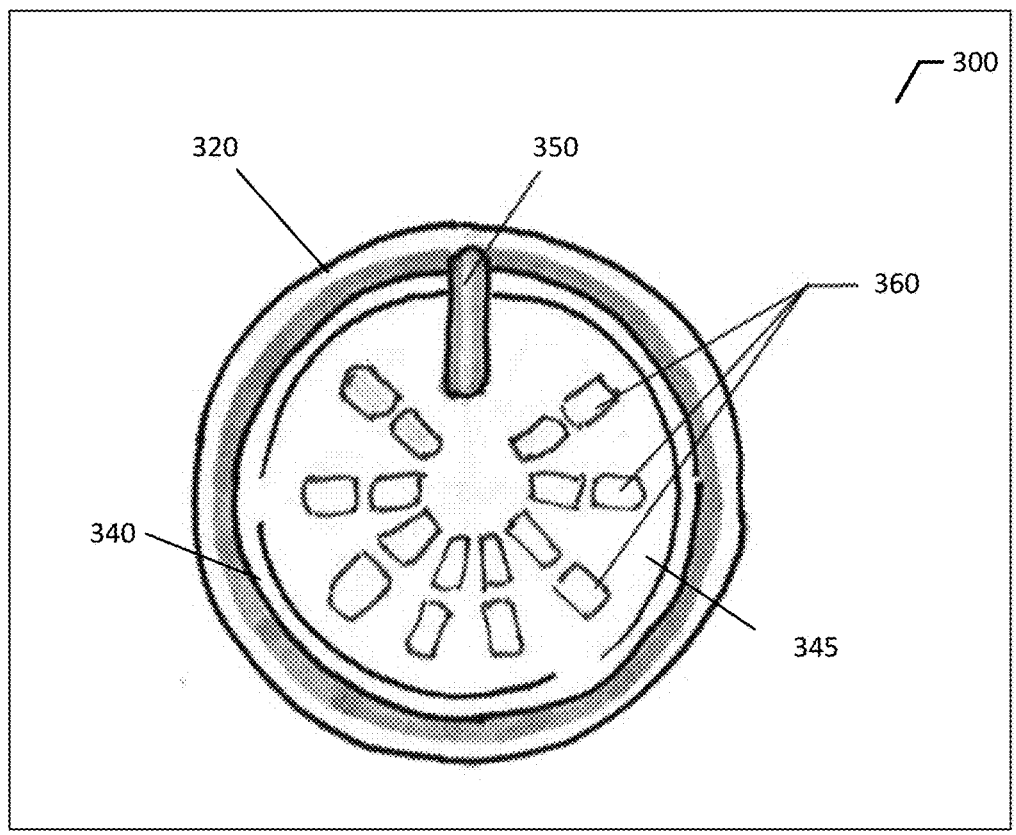
FIG. 3B is a bottom view illustration of an example of the puck of FIG. 3A according to an embodiment of the present disclosure.

An example of an embodiment of puck 110 is illustrated in FIG. 3A (side view) and FIG. 3B (bottom view).

FIG. 3A illustrates a side view of an example of an embodiment of a puck 300 shaped for snap-fit placement in a receptacle 120. Puck 300 includes three portions 320, 330, 340, where portion 330 is between portions 320 and 340. An outer diameter of portion 320 is greater than an outer diameter of portion 340, and the outer diameter of portion 340 is greater than an outer diameter of portion 330. Either portion 340 has some flexibility, or receptacle 120 has some flexibility, such that portion 340 may pass through an opening of receptacle 120 with an outer diameter that is less than the outer diameter of portion 340 but greater than the outer diameter of portion 330. In this way, puck 300 may be snapped into the associated receptacle by a slight deformation of the portion 340 or a slight deformation of the opening of receptacle 120, allowing portion 340 to pass and portion 330 to rest in the opening. Puck 300 further includes an alignment notch 350 for proper positioning of puck 300 in receptacle 120. In the embodiment illustrated in FIG. 3A, alignment notch 350 extends through portions 330 and 340, and slightly into portion 320. When puck 330 is placed in receptacle 120, a bottom surface 345 of portion 340 is positioned facing receptacle 120.

Puck 300 includes a housing (e.g., portions 320, 330, 340) with various electronic components inside, as discussed elsewhere in the present disclosure. The housing may be sealed, so that it is water and humidity resistant, or waterproof FIG. 3B illustrates a bottom view of puck 300, where the term "bottom" is relative to the orientation of FIG. 3A. Because the outer diameter of portion 320 is greater than the outer diameter of portion 340, an annular view of portion 320 surrounding portion 340 can be seen from the bottom of puck 300. Alignment notch 350 extends horizontally across the bottom of puck 300, in addition to extending vertically (FIG. 3A). Puck 300 includes contact areas 360, which may be protrusions, pads, or recesses, or a combination thereof. Contact areas 360 make physical contact with respective areas of receptacle 120, and some or all of contact areas 360 may also make electrical contact with the respective areas of receptacle 120.

In the embodiment of FIGS. 3A, 3B, puck 300 has a generally circular form in a bottom view, and contact areas 360 are arranged along generally concentric circles. In other embodiments, puck 300 has as a different form in a bottom view, such as elliptical, square, rectangular, or polygonal. Further, positioning, number and size of contact areas 360 within the scope of the present disclosure may be different than illustrated in FIG. 3B.

Figure 4A:
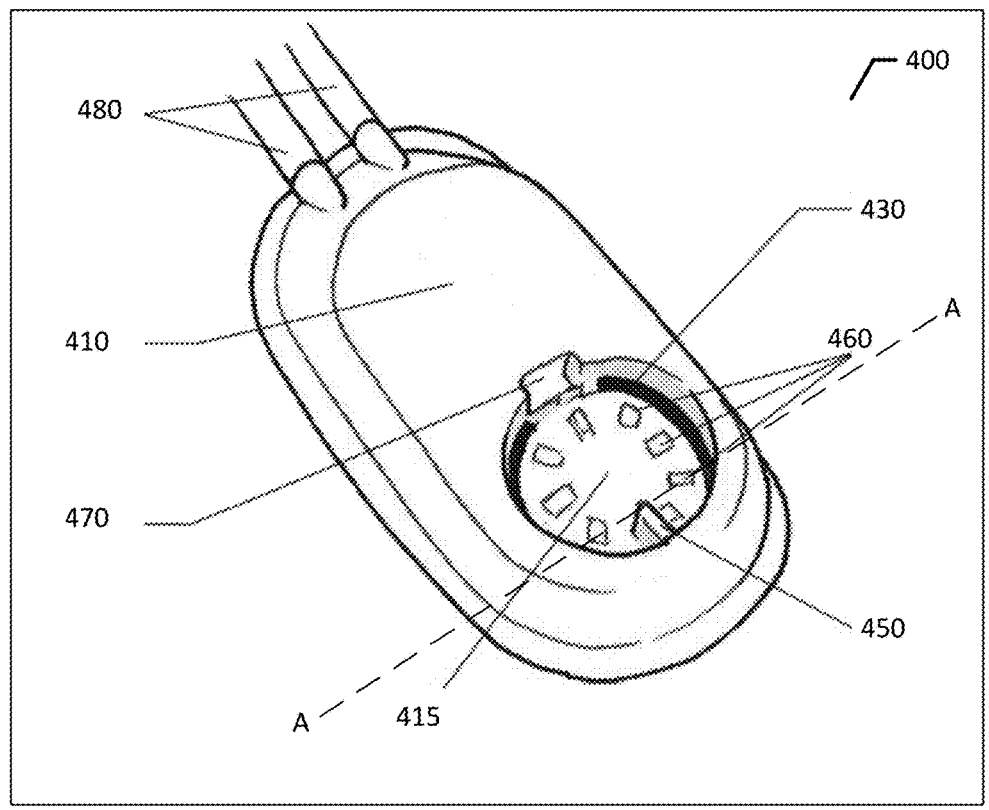
FIG. 4A is a perspective view illustration of an example of a receptacle according to an embodiment of the present disclosure.

An example of an embodiment of receptacle 120 is illustrated in FIGS. 4A (perspective view) and 4B (end view).

FIG. 4A illustrates a perspective view of an example of an embodiment of a receptacle 400 with a configuration corresponding in some respects to puck 300 of FIGS. 3A, 3B, and thus puck 300 will be referred to in the following description by way of non-limiting example. Receptacle 400 includes a casing or housing 410 that defines a cavity 415 into which puck 300 is placed. A ring 430 (or partial ring, or segments of a ring) is positioned to provide a snap fit between receptacle 400 and puck 300, such that portion 340 of puck 300 pushes past ring 430 of receptacle 400, and ring 430 of receptacle 400 rests in portion 330 of puck 300. Alignment protrusion 450 is connected to (or is part of) casing or housing 410, extends horizontally into cavity 415, and vertically to (or beyond) ring 430. When puck 300 is placed in receptacle 400, alignment protrusion 450 of receptacle 400 is positioned within alignment notch 350 of puck 300.

Receptacle 400 further includes contact areas 460. When puck 300 is placed in receptacle 400, some of contact areas 360 of puck 300 make physical contact with respective contact areas 460 of receptacle 400; further, some of contact areas 360 of puck 300 make electrical contact with respective contact areas 460 of receptacle 400. Puck 300 may have more contact areas 360 than receptacle 400 has contact areas 460, because receptacle 400 is for a specific use, whereas puck 300 is agnostic to use. In this way, one puck 300 may be used with a variety of specific-use receptacles 400.

Receptacle 400 further includes an optional latch 470 that is positioned over puck 300 to hold puck 300 in place within cavity 415 of receptacle 400, and may be moved to allow for removal of puck 300 from receptacle 400.

Receptacle 400 further includes optional wiring 480 for connection to sensors of an associated article 130. In one or more embodiments, the sensors are contained within casing or housing 410, and wiring 480 is not implemented.

Figure 4B:
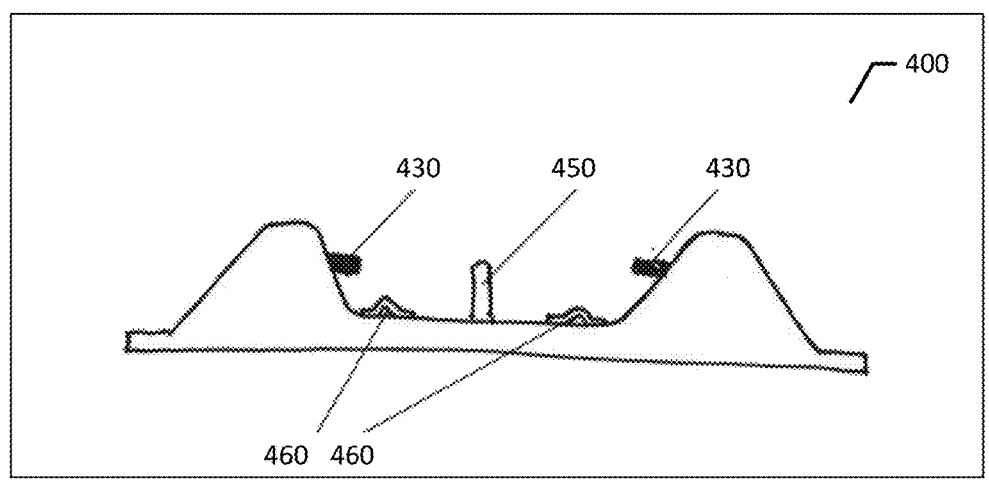
FIG. 4B is an end view illustration of the receptacle of FIG. 4A according to an embodiment of the present disclosure.

FIG. 4B illustrates receptacle 400 from a cross-sectional view along line A-A in FIG. 4A. In this view, a tapering profile of cavity 415 is evident. The tapering profile matches a tapering profile of puck 300 (FIG. 3A). As noted above, when puck 300 is placed in receptacle 400, ring 430 of receptacle 400 is positioned in portion 330 of puck 300, and alignment protrusion 450 of receptacle 400 is positioned within alignment notch 350 of puck 300. Contact areas 460 are illustrated in FIG. 4B as protrusions; however, contact areas 460 may instead be pads or recesses. The form of contact areas 460 of receptacle 400 and contact areas 360 of puck 300 are complimentary, such as pad-to-pad, protrusion-to-recess, or recess-to-protrusion. In one or more embodiments, contact areas 460 and 360 each include a combination of pads, protrusions, and recesses.

FIGS. 3A, 3B, 4A and 4B together thus describe a mating pair of puck 300 and receptacle 400 by way of example. Many other configurations are within the scope of this disclosure.

Figures 5A, 5B:
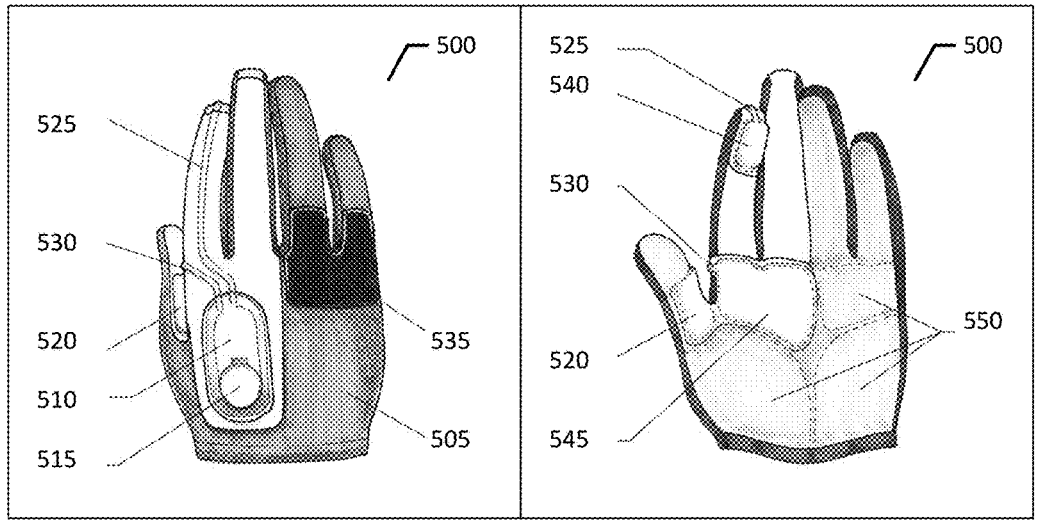
FIGS. 5A, 5B illustrate a glove according to an embodiment of the present disclosure.

FIGS. 5A, 5B illustrate an implementation of article 130 in the form of a glove 500. Glove 500 includes a receptacle 510 (e.g., receptacle 120 or 400) positioned thereon, and a puck 515 (e.g., puck 110 or 300) placed within receptacle 510. FIG. 5A illustrates a back side of a right glove 500, and FIG. 5B illustrates a palm side of a left glove 500, where the right and left gloves 500 are constructed in mirror image with respect to each other.

Referring to FIGS. 5A and 5B together, glove 500 includes a glove body 505 of a flexible material, upon which receptacle 510 is permanently or semi-permanently attached. In one or more embodiments, receptacle 510 is detachable, so that glove 500 may be laundered. In other embodiments, receptacle 510 may be laundered with glove 500. Puck 515 is shown placed in receptacle 510, and is removable. Wiring 525 electrically connects a fingertip sensor 540 to receptacle 510. Wiring 530 electrically connects a palm sensor 545 and a thumb sensor 520 to receptacle 510. In the embodiment of glove 500, portions 535 and 550 are structural reinforcements that do not contain sensors.

Figures 6A, 6B:
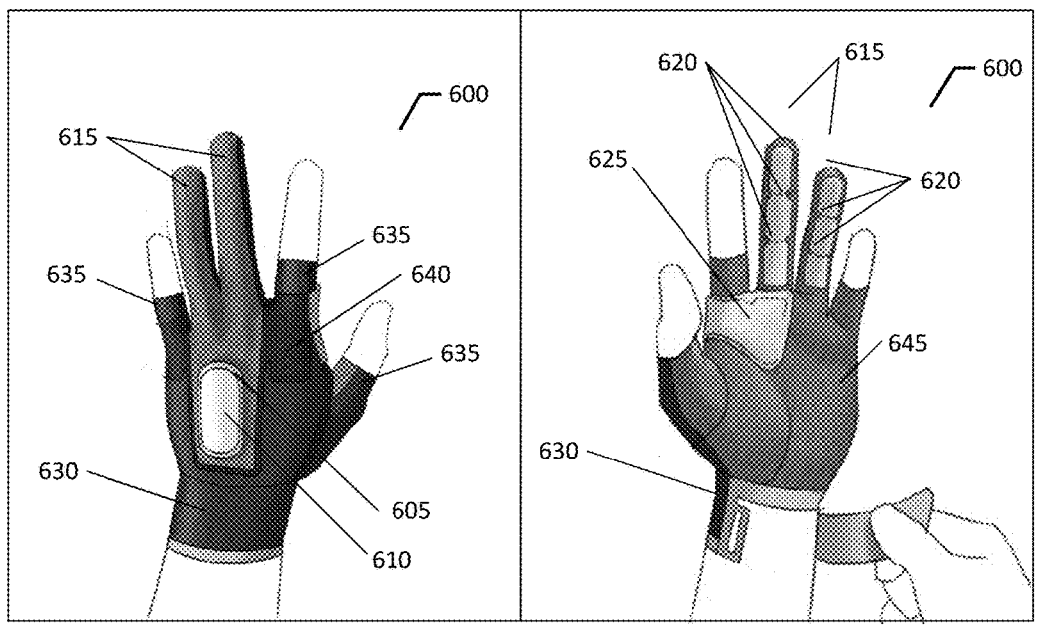
FIGS. 6A, 6B illustrate a glove according to another embodiment of the present disclosure.

FIGS. 6A, 6B illustrate a different implementation of article 130 as a glove 600. Glove 600 includes a receptacle 605 and a puck 610 placed therein. FIG. 6A illustrates a back side of a left glove 600, and FIG. 6B illustrates a palm side of the left glove 600. A right glove 600 (not shown) may be a mirror image of the left glove 600. Referring to FIGS. 6A and 6B together, rather than thumb sensor 520 and fingertip sensor 540 as in glove 500, glove 600 includes two finger portions 615, each with one or more sensors 620. Similar to palm sensor 545 of glove 500, glove 600 includes palm sensor 625. Glove 600 further includes an optional wrist strap 630. In one or more embodiments, glove 600 may include material along fingers/thumb not covered by finger portions 615; however, as illustrated in the embodiment of FIGS. 6A, 6B, a portion 635 of the glove 600 material may leave the remaining fingers/thumb exposed. In one or more embodiments, glove 600 includes a mesh material 640 over portions of glove 600 for breathability. In one or more embodiments, a palm grip 645 is perforated leather to provide improved grip. In one or more embodiments, wrist strap 630 is a compression material.

Figure 7:
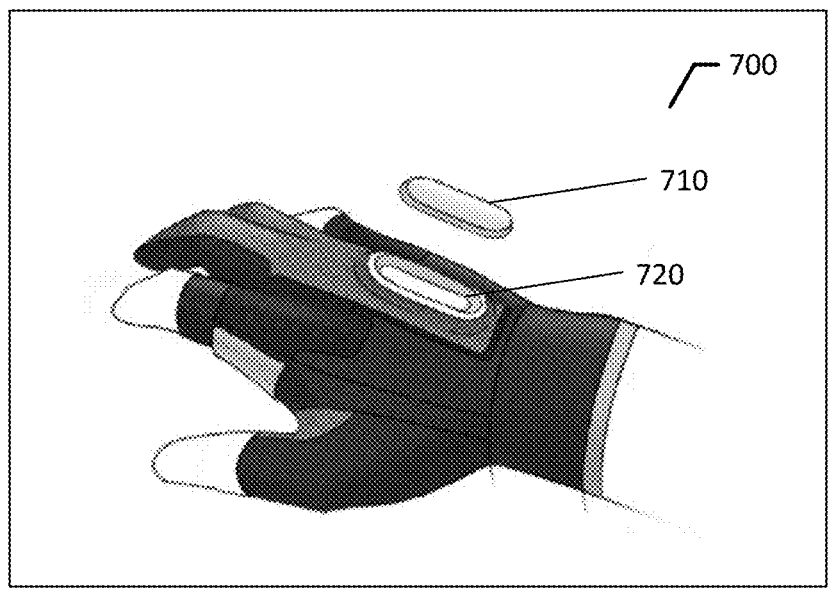
FIG. 7 illustrates a removable puck according to an embodiment of the present disclosure.

FIG. 7 illustrates a glove 700 similar to the glove 600 of FIGS. 6A, 6B. As shown, a puck 710 is removable from a receptacle 720 of the glove 700.

Figure 8:
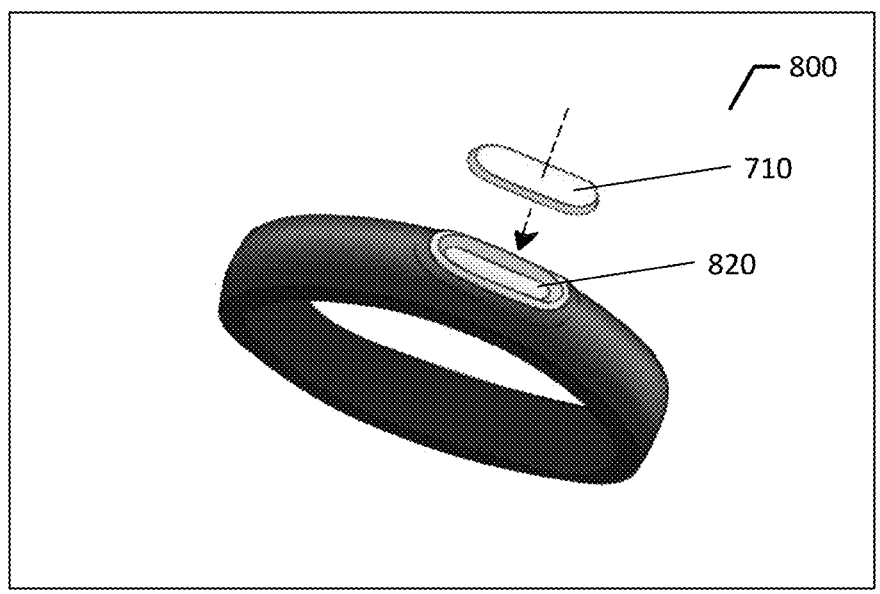
FIG. 8 illustrates placing a puck into a wristband article.

FIG. 8 illustrates a wristband 800 (or armband or legband). As shown, puck 710 (FIG. 7) may be placed in a receptacle 820 of wristband 800. In one or more embodiments, wristband 800 is an activity-specific article 130, such as a pedometer with sensors for measuring arm swing, or a bio-feedback device with sensors for measuring heart rate, blood pressure, oxygen level, and such. In one or more embodiments, wristband 800 includes a computing device 140. In such embodiments, information received by puck 710 during placement in receptacle 720 of glove 700 may be transferred to wristband 820. In turn, wristband 820 may provide the information from puck 710 via network 150 to another computing device 140. For example, wristband 820 may provide the information via a local area network such as Wi-Fi or Bluetooth to a smart phone, or via an Internet protocol to a remote computer of the Internet. In one or more embodiments, puck 710 includes a capability to provide information wirelessly over a local area network.

Figure 9:
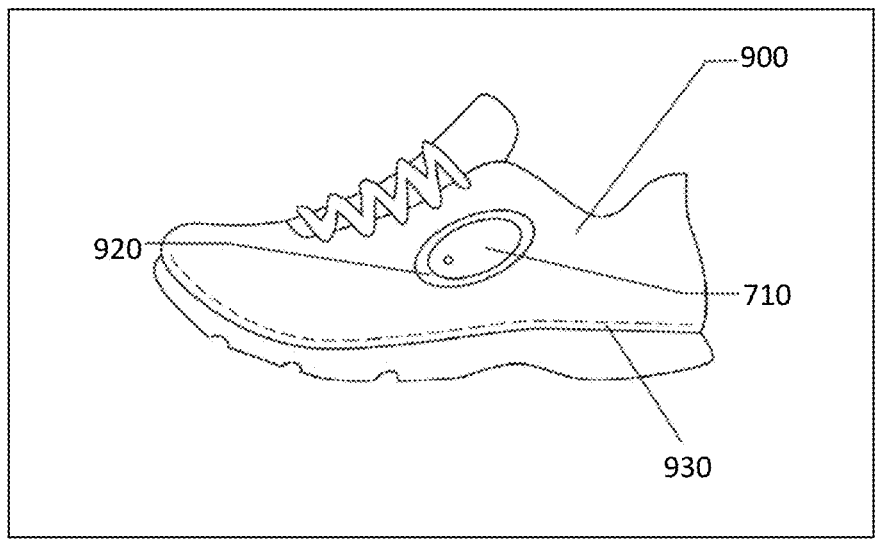
FIG. 9 illustrates a shoe article according to an embodiment of the present disclosure.
Figure 10:
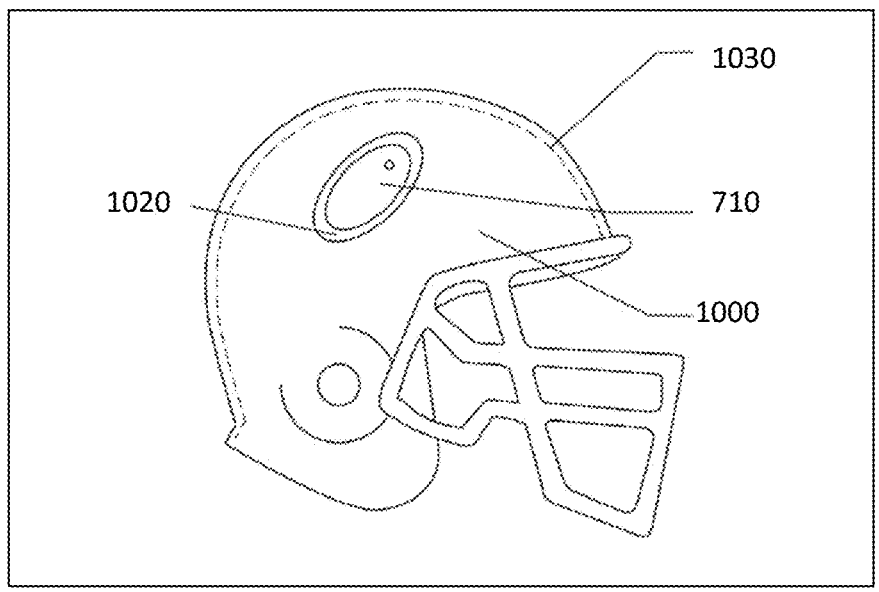
FIG. 10 illustrates a helmet article according to an embodiment of the present disclosure.

FIGS. 9 and 10 illustrate that puck 710 may be removed from wristband 800 and placed in other receptacles, such as receptacle 920 of shoe 900, where sensors include pressure sensors 930 in a shoe insert or shoe sole; or such as receptacle 1020 in helmet 1000, where sensors include force sensors 1030 in a lining of the helmet 1000.

Figure 11:
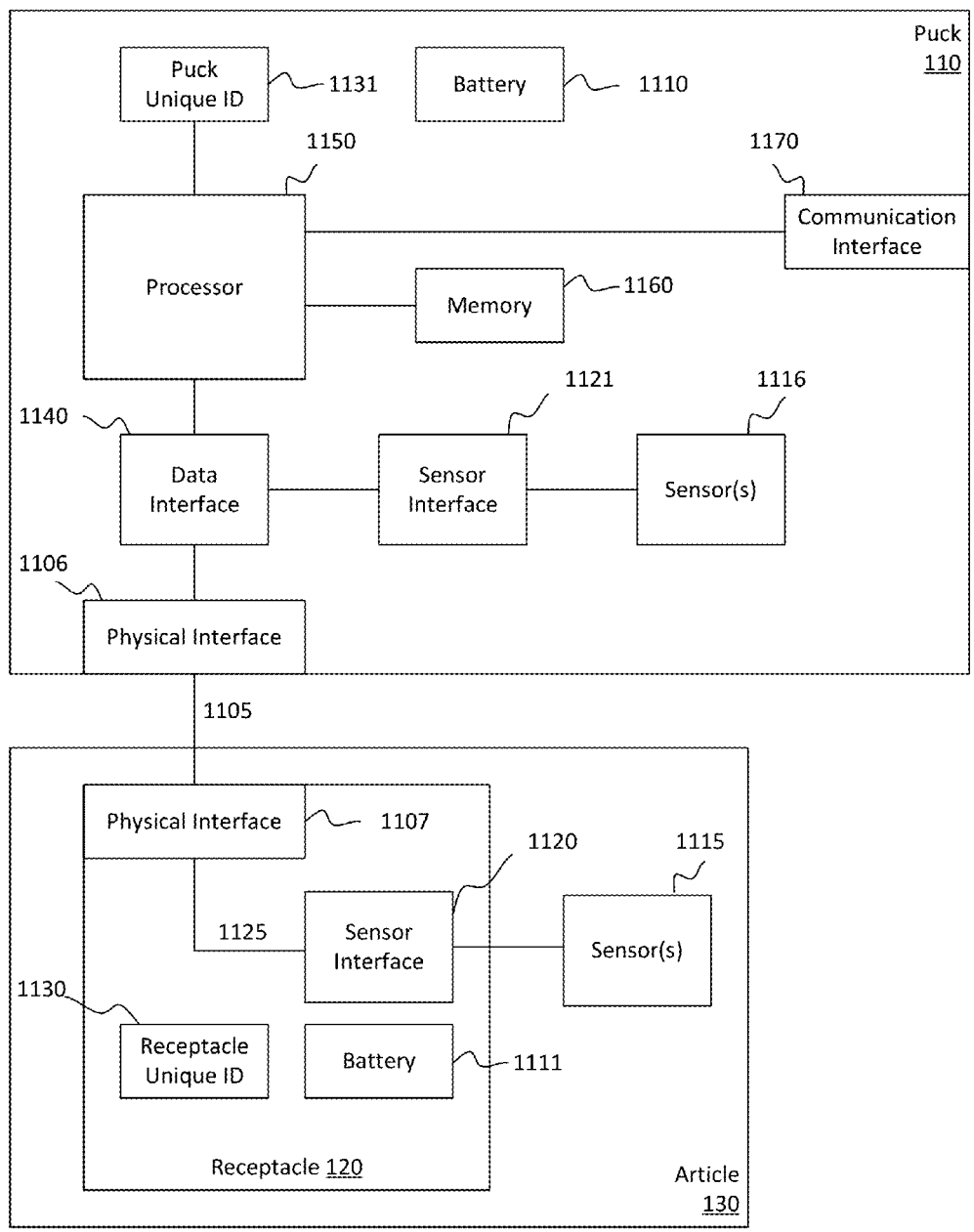
FIG. 11 is a block diagram of components of a physical activity monitoring system according to an embodiment of the present disclosure.

FIG. 11 illustrates in block diagram form how components of modular physical activity monitoring system 100 may interact with each other, in accordance with an embodiment of the present disclosure. Puck 110 is represented as being physically connected to (placed in) receptacle 120 by way of line 1105 representing physical connection between puck 110 and receptacle 120 positioned on article 130. Line 1105 may also represent electrical interconnection. Thus, physical interface 1106 of puck 110 is in physical (and electrical) contact with physical interface 1107 of receptacle 120. Physical contact may be through alignment of pads, protrusions, or recesses, such as pad-on-pad or protrusion-in-recess contact, as described above.

Puck 110 includes a rechargeable battery 1110. Receptacle 120 may receive power through physical interface 1107 from puck 110, or may include a rechargeable battery 1111. To reduce a size of puck 110 and receptacle 120, small-footprint batteries are used. Some small-footprint batteries have low charge storage capability. Accordingly, a power management scheme may be implemented, such that one or both of puck 110 and receptacle 120 are moved between power states according to an amount of power currently demanded, or to force lower power usage when a battery 1110, 1111 is approaching a low charge state. For example, a subject's rate of change of motion may be very slow relative to a speed of a microprocessor, and thus, circuitry incorporated into puck 110 and/or receptacle 120 may be put into a low power state between sensor readings.

When puck 110 and receptacle 120 are disengaged, there may not be a reason to keep one or both powered up, and thus one or both are powered down to a lower power state, or powered off. In one or more embodiments, physical contact between physical interfaces 1106, 1107 engages a mechanical switch that activates power or a change in power level for one or both of puck 110 and receptacle 120. In one or more embodiments, physical contact between physical interfaces 1106, 1107 engages an electrical switch that activates power or a change in power level for one or both of puck 110 and receptacle 120.

In one or more embodiments, one or both of batteries 1110, 1111 are recharged by harvesting energy from a motion of the subject.

Article 130 includes one or more sensors 1115. Some examples of sensors are described below. Sensors 1115 may output measurements in digital or analog form, such as digital words representing an analog value, analog signals whose frequencies represent discrete values, analog signals whose magnitudes represent discrete values, analog signals that change with a changing sensed parameter, or digital signals representing a presence or absence of a parameter. A sensor interface 1120 receives the analog or digital signals, and may apply filtering, smoothing, zero offsetting, normalization, or other signal pre-processing prior to providing information related to the signals to physical interface 1107. In one or more embodiments, sensor interface 1120 is implemented in hardware, and outputs of sensor interface 1120 are hardwired to physical interface 1107 via traces/wires 1125. In one or more embodiments, sensor interface 1120 includes a computing device, such as a microprocessor, that performs digital signal processing to pre-process the signals, and then provides information related to the signals to physical interface 1107 over traces/wires 1125 connected to physical interface 1107, such as a serial or parallel interface with traces/wires 1125, or through dedicated or switched input/output pins connected to traces/wires 1125.

Receptacle 120 includes a unique identifier (UID) 1130, that identifies receptacle 120, for example, by one or more of model number, serial number, manufacture date, intended activity, type of article to which it is attached, sensor types, sensor interface information, or other identifying information. The UID 1130 is provided to puck 110 when puck 110 is placed into receptacle 120. In one or more embodiments, puck 110 may determine from UID 1130 a number and type of contact areas (e.g., contact areas 460 in FIG. 4A) of receptacle 120, and signal types expected at the contact areas. In one or more embodiments, the contact areas of each receptacle 120 in a physical activity monitoring system 100 are the same in number, type, and expected signal configurations. In other embodiments, different receptacles 120 have different number, type, and expected signal configurations. In one or more embodiments, puck 110 stamps data received from receptacle 120 with UID 1130. In this manner, as puck 110 is moved between receptacles 120, stored data may be identified as being received from a specific receptacle 120. Stored data may further be time-stamped.

As noted above, article 130 may include multiple receptacles 120. Thus, it may be envisioned that one puck 110 may be moved between multiple receptacles 120 of an article 130, or multiple pucks 110 may be moved between multiple receptacles 120 of an article 130. Alternatively, each of multiple receptacles 120 of an article 130 may be populated with a respective puck 110.

Puck 110 includes activity-agnostic sensors 1116, which are agnostic to the use of receptacle 120 or of article 130. For example, article 130 may be a knee brace, and sensors 1115 of the knee brace provide data specific to the knee, such as pressure, bend, angle, and acoustic information. Sensor 1115 data specific to the knee is provided to sensor interface 1120, and then the data, or information related to the data, is provided by sensor interface 1120 to puck 110 through traces/wires 1125 and physical interfaces 1106, 1107. Meanwhile, a sensor interface 1121 of puck 110 gathers generic (e.g., not specific to the knee) information or data from sensors 1116, such as, for example, accelerometer, gyroscope, or magnetometer information for determining acceleration, velocity, gravitational force, relative motion, tilt, or orientation with respect to puck 110.

Sensors 1116 may output measurements in digital or analog form, such as digital words representing an analog value, analog signals whose frequencies represent discrete values, analog signals whose magnitudes represent discrete values, analog signals that change with a changing sensed parameter, or digital signals representing a presence or absence of a parameter. Sensor interface 1121 receives the analog or digital signals, and may apply filtering, smoothing, zero offsetting, normalization, or other signal pre-processing. In one or more embodiments, sensor interface 1121 is implemented in hardware, and outputs of sensor interface 1121 are hardwired to data interface 1140. In one or more embodiments, sensor interface 1121 includes a computing device, such as a microprocessor, that performs digital signal processing to pre-process the signals, and then provides information related to the signals to data interface 1140, such as over a serial or parallel interface, or through dedicated or switched input/output pins.

Information or data from sensor interface 1121 may subsequently be used with information from sensor interface 1120, such as for verification of data received, or for reconstruction of movement, for example.

Information or data received from sensor interface 1120 through physical interfaces 1106, 1107 is provided to data interface 1140. Information received from sensor interface 1121 is also provided to data interface 1140. A form of the information received at data interface 1140 is provided to a processor 1150.

Data interface 1140 includes circuitry for converting the information received at data interface 1140 into a format suitable for use by processor 1150. In one or more embodiments, the circuity includes one or more filters, such as low-pass, band-pass, or high-pass filters, implemented in hardware or software (e.g., in a secondary processor or an FPGA). In one or more embodiments, the circuitry includes analog-to-digital (A/D) and/or digital-to-analog (D/A) converters. In one or more embodiments, the circuitry includes level-shifting and/or zero offsetting capability. In one or more embodiments, the circuitry includes a capability to convert from data received in one form to data received in another form, such as converting from parallel data to serial data, serial data to parallel data, data formatted in a first protocol to data formatted in a second protocol, and so forth. Further, in one or more embodiments, data interface 1140 performs data fusion.

In one or more embodiments, data interface 1140 time stamps information received. For example, data interface 1140 may stamp information from sensor interfaces 1120, 1121 with the time that it was received at data interface 1140. In one or more embodiments, data interface 1140 stamps information from sensor interface 1120 with UID 1130 of receptacle 120 from which it was received, and stamps information from sensor interface 1121 with UID 1131 of puck 110.

In other embodiments, time stamps and/or UID 1130, 1131 stamps are applied by processor 1150 instead of by data interface 1140. In yet further embodiments, one or both of time stamps and UID 1130, 1131 stamps are not applied.

Processor 1150 receives information provided by data interface 1140, and stores the information in a memory 1160 (such as described with respect to memory 220 in FIG. 2). In one or more embodiments, processor 1150 includes a direct memory access (DMA) controller that automatically stores information from data interface 1140 to memory 1160, or from sensor interface 1121 to memory 1160. Processor 1150 may pre-process information received from data interface 1140, such as by frequency band filtering (e.g., low-pass, band-pass, or high-pass filtering), decimating or otherwise down-sampling, smoothing, integrating or otherwise averaging, normalizing, error checking, validity checking (e.g., "sanity" checking), and so forth. Such pre-processing may be performed on information as it is received (e.g., in near real time), or may be performed on information retrieved from memory 1160. The term near real time in this context accounts for system and processing delays.

Processor 1150 provides information received from data interface 1140 to a communication interface 1170 (such as described with respect to communication interface 240 in FIG. 2). Processor 1150 provides the information formatted according to the protocol used for communication interface 1170. For example, the information may be provided as data packets with or without headers, as serial data words, as parallel data words, or other formats. In one or more embodiments, near real time information is provided to communication interface 1170. In one or more embodiments, processor 1150 provides the information stored in memory 1160 without further data processing; in other embodiments, processor 1150 further processes the information prior to providing the information to communication interface 1170. For example, processor 1150 may perform data fusion, and/or may apply the information to a model to identify activities (e.g., deep knee bends in the example of the knee brace), and send information related to the identified activities to the communication interface 1170. Such information may include activity, number of repetitions, repetition rate, time between repetitions, increasing or decreasing time between repetitions, or other such information useful for tracking activity.

In one or more embodiments, communication interface 1170 is wireless, and thus near-real time information may be gathered and processed. In one or more embodiments, puck 110 includes an audio, visual, or haptic device that provides feedback to a wearer of article 130. For example, a computing device 140 within physical activity monitoring system 100 may receive information from puck 110, identify an activity being performed, and provide audio, visual, or haptic feedback to the wearer indicating whether the activity is being performed correctly.

In one or more embodiments, puck 110 is placed in an upload receptacle to provide information from memory 1160 to a computing device 140 through a wired or wireless connection. An upload receptacle may include multiple bays for wired connection, to allow for uploading data from multiple pucks 110 concurrently. The upload receptacle may include wired or wireless charging to recharge puck(s) 110.

Communication from puck 110 to computing device 140 may be encrypted, or may include other data security measures, such as for limiting access to personal information to only those designated for access.

In one or more embodiments, puck 110 includes a sensor 1116 for detecting pulse. Characteristics of a subject's pulse may be matched to characteristics stored in a database to identify whether the subject is the person registered to puck 110.

By way of an example of a physical activity monitoring system 100, an embodiment is next described in which physical activity monitoring system 100 is used to improve training of a hypothetical subject who is a weightlifter and also a bicycle enthusiast. In this example, the subject is monitored remotely by a physical trainer. On a first day, the subject is provided with a list of weightlifting activities to perform in a given sequence with a defined number of repetitions. On the first day, the subject wears two gloves, described by way of example as gloves 600 illustrated in FIGS. 6A, 6B. Each glove 600 incorporates sensors 620, 625 coupled to receptacle 605. On the first day, a puck 610 is placed in each glove 600, such that sensor 620, 625 data may be received at both hands. Sensors 620, 625 include pressure or force sensors, so that the subject's grip strength may be monitored, among other things. The subject progresses through the list of weightlifting activities, and when finished, removes both pucks 110, and downloads data from both pucks 110 through communication interface 1170 to a smart phone, tablet, or other computing device. The subject then submits the data from the computing device to the trainer, such as via email, a data exchange site, or submission into website associated with the trainer or with physical activity monitoring system 100. The trainer analyzes the data, such as to see whether instructions were followed, whether the subject was able to perform the list of activities, to determine repetition rates, to identify a weak arm or hand, or other analyses applicable to the training The trainer prepares a list of activities for the second day, and provides the list to the subject.

Continuing with the example, on the second day, the trainer wishes to receive information from hands and knees to verify correct motion or identify stress points, but knows that the subject has no more than two pucks 110. Thus, on the second day, the subject is directed to use one puck 110 in the glove of the weak arm, and one puck 110 in a biker knee brace on the same side of the body. At the end of the second day, the subject provides the data from pucks 110 to the trainer, and the trainer analyzes the data. On the third day, the trainer instructs the subject to go biking, wearing two biker knee braces, and placing one of the subject's two pucks 110 in each biker knee brace. At the end of the third day, the subject provides the data from pucks 110 to the trainer, and the trainer analyzes the data to identify whether the biking is augmenting or detracting from the weight training, such as whether the joints are becoming overstressed from similar use in both weightlifting and biking Pucks 110 each provide activity-agnostic information to augment the information received from gloves 600 and the biker knee braces. Thus, whether placed in glove 600 or placed in a biker knee brace, puck 110 gathers activity-agnostic information from internal sensors 1116, such as three-dimensional acceleration data or biological data (e.g., pulse or temperature). When the activity-agnostic information from puck 110 and activity-specific information (such as data from sensors 1115 in weightlifting gloves) is combined, the result is a more detailed picture of the activity performed.

The example of the hypothetical weightlifting/biking subject provides one scenario for use of physical activity monitoring system 100. Many other scenarios are within the scope of the present disclosure. Such scenarios include, but are not limited to, physical therapy regimens, training for synchronous sports, proof of activity performed, analysis of workplace injury-inducing tasks, detection of injury-inducing movements, modeling of human behavior, teaching of robotic systems through mimicking of movements, providing activity models for character animation, interactive gaming, remote manipulation of tools (e.g., manufacturing or surgical) or vehicles (e.g., drones and bomb disposal units), retraining human behavior following a stroke, and many other scenarios.

Figure 12:
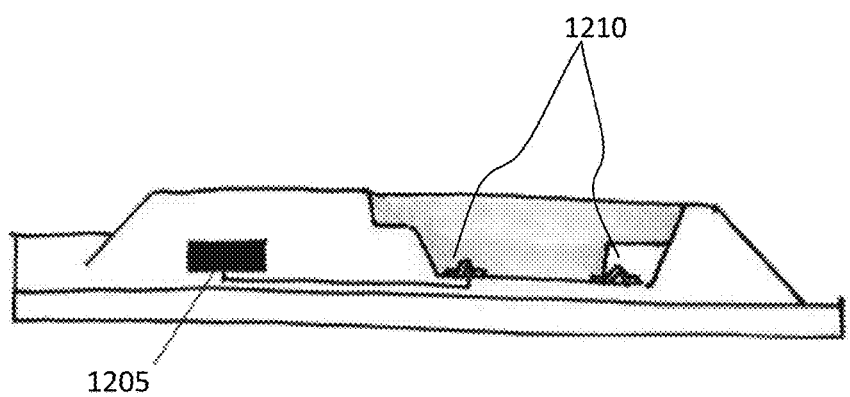
FIG. 12 is an illustration of a unique ID device according to an embodiment of the present disclosure.

FIG. 12 illustrates an example of a receptacle 120 including a programmable (and possibly reprogrammable) UID device 1205. UID device 1205 may be electrically connected to one or more contact areas 1210 (similar to contact areas 460 in FIG. 4B) of receptacle 120 as shown. In one or more embodiments, UID device 1205 is a radio frequency identification (RFID) chip or screen print. In one or more embodiments, UID 1205 is an ASIC. In one or more embodiments, UID device 1205 is a programmable resistor or set of programmable resistors, and the resistive value is read by puck 110 through contact areas 1210. In such embodiments, a number of programmable resistors, or a resolution of the resistor value of a programmable resistor, provides sufficient different UIDs for the application, such as sufficient different UIDs for each type of receptacle 120, for each receptacle 120 manufactured, or for each receptacle 120 provided to a particular user.

Sensors

Referring back to FIG. 11, article 130 is, or includes, a flexible textile, such as a flexible upper or flexible inner sole for a shoe, a flexible shirt material with stiff elbow guards for skateboarding, a flexible pant material for skiing, a flexible body suit for surfing, a flexible inner surface material of a helmet, and so forth. Article 130, or portions thereof, are washable.

Activity-specific sensors 1115 are incorporated into or onto the material of article 130. Examples of sensors 1115 include piezoresistive, piezoelectric, photoelectric, capacitive or inductive sensors, and resistive thermal detectors (RTD, also known as resistive temperature detectors). Sensors 1115 may be used to detect, for example, electrodermal activity (such as skin conductance, galvanic skin response, electrodermal response, psychogalvanic reflex, skin conductance response, and skin conductance level), muscle cell electrical potential (such as for electromyography), proximity, luminescence, heart rate, temperature, touch, force, motion and pressure.

In one or more embodiments, a piezoelectric ink or paint is used to form sensor 1115. In one or more embodiments, a piezoresistive ink is disposed on a portion of the material of article 130, or a piezoresistive material is used for a portion of, or all of, article 130. Resistance can be measured with resistor ladders, Wheatstone bridges, matrix (row and/or column) threshold sensing, or other techniques. Resistance sensing may be absolute or relative. In either case, resistivity of sensor 1115 may be characterized, and measurements adjusted according to a calibration determined from the characterization.

Piezoresistive or piezoelectric sensors may be formed using multiple alternating layers of conductive material. For example, piezoresistive material can include conductive fibers, conductive fragments: when the piezoresistive material is compressed, the conductive fibers or fragments become closer together, which changes a resistance of the material locally to where the material was compressed. Conductors or conductive layers on both sides of the material are used to detect the resistance. Layers of such piezoresistive material may be stacked with an insulating material between to provide additional range, sensitivity or resolution for the intended application.

For example, different piezo ink formulas have different impedance curves, some having good sensitivity for lighter weights, and others having little sensitivity for lighter weights but useful over a wide range of weights. Thus, different inks could be used alone to achieve, for example, good sensitivity for lighter weights, or sensitivity over a wide range of weights. Alternatively, a combination of the inks can be used, such as on different layers, or side-by-side, to achieve a desired sensitivity for a given weight range.

A coating may be applied over the conductive fibers or material, to electrically insulate the conductive fibers or material, as well as to protect the conductive fibers or material from degradation during use and laundering.

A Prototype of an Embodiment

Figure 13A:
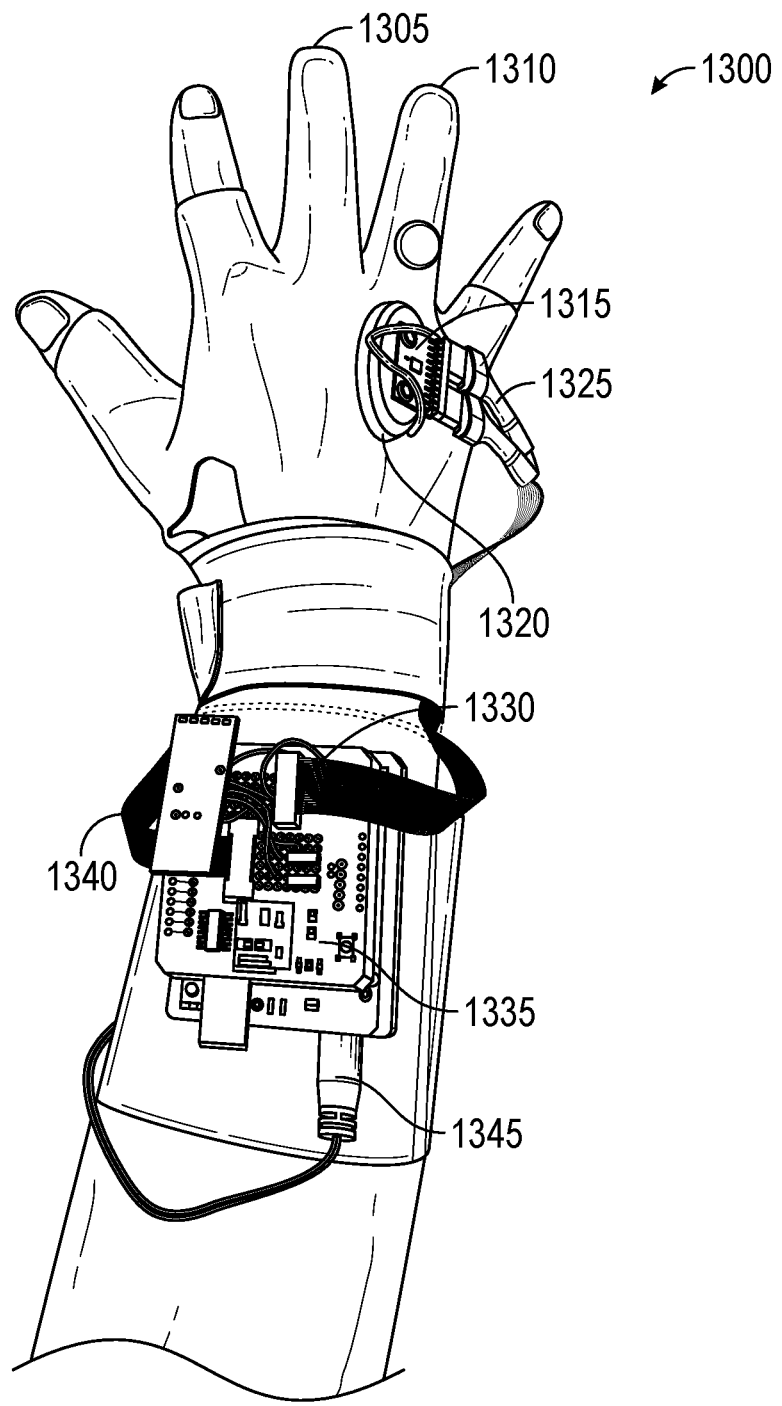
FIGS. 13A, 13B illustrate a prototype weightlifting glove according to an embodiment of the present disclosure.
Figure 13B:
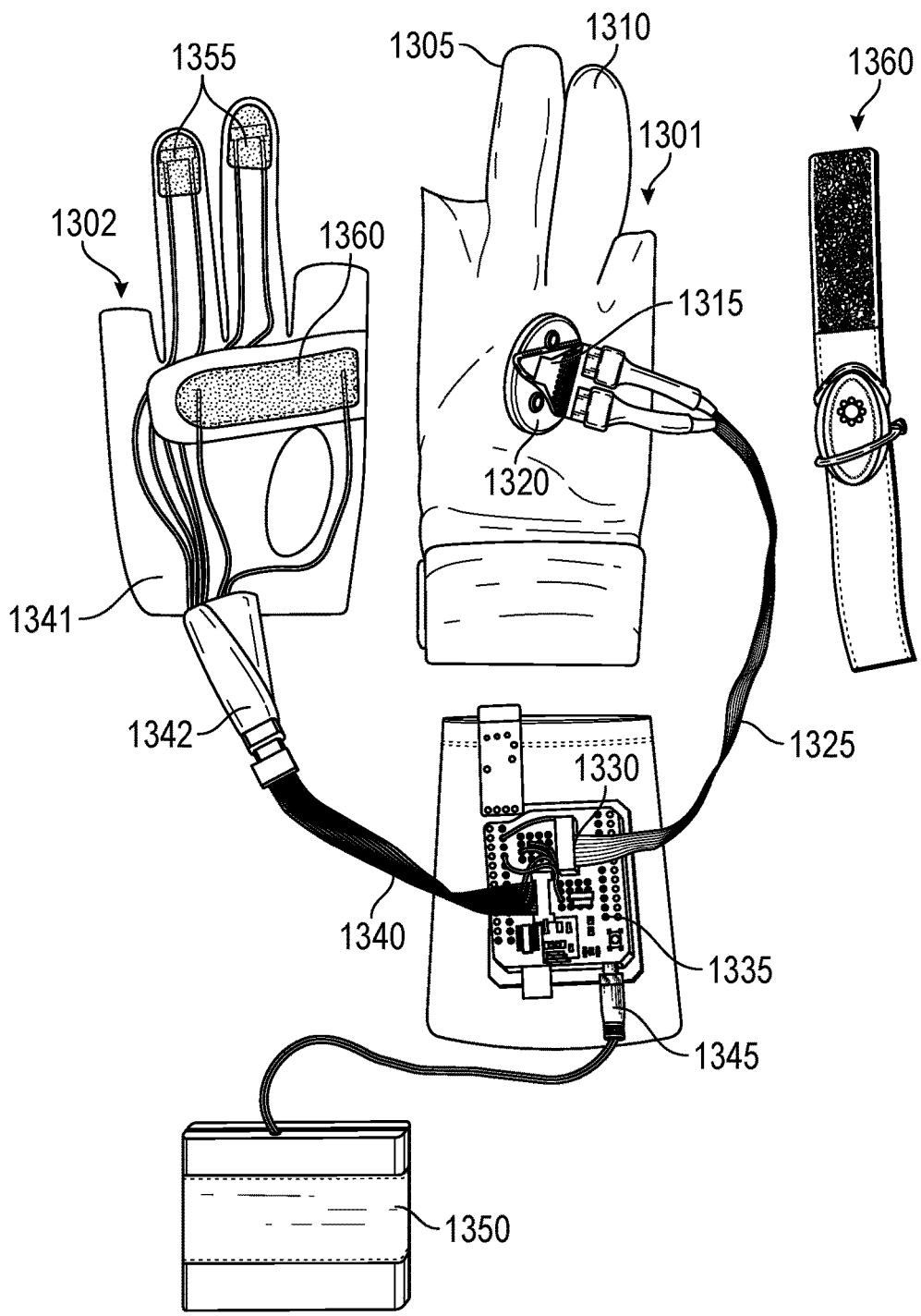
Figure 13C:
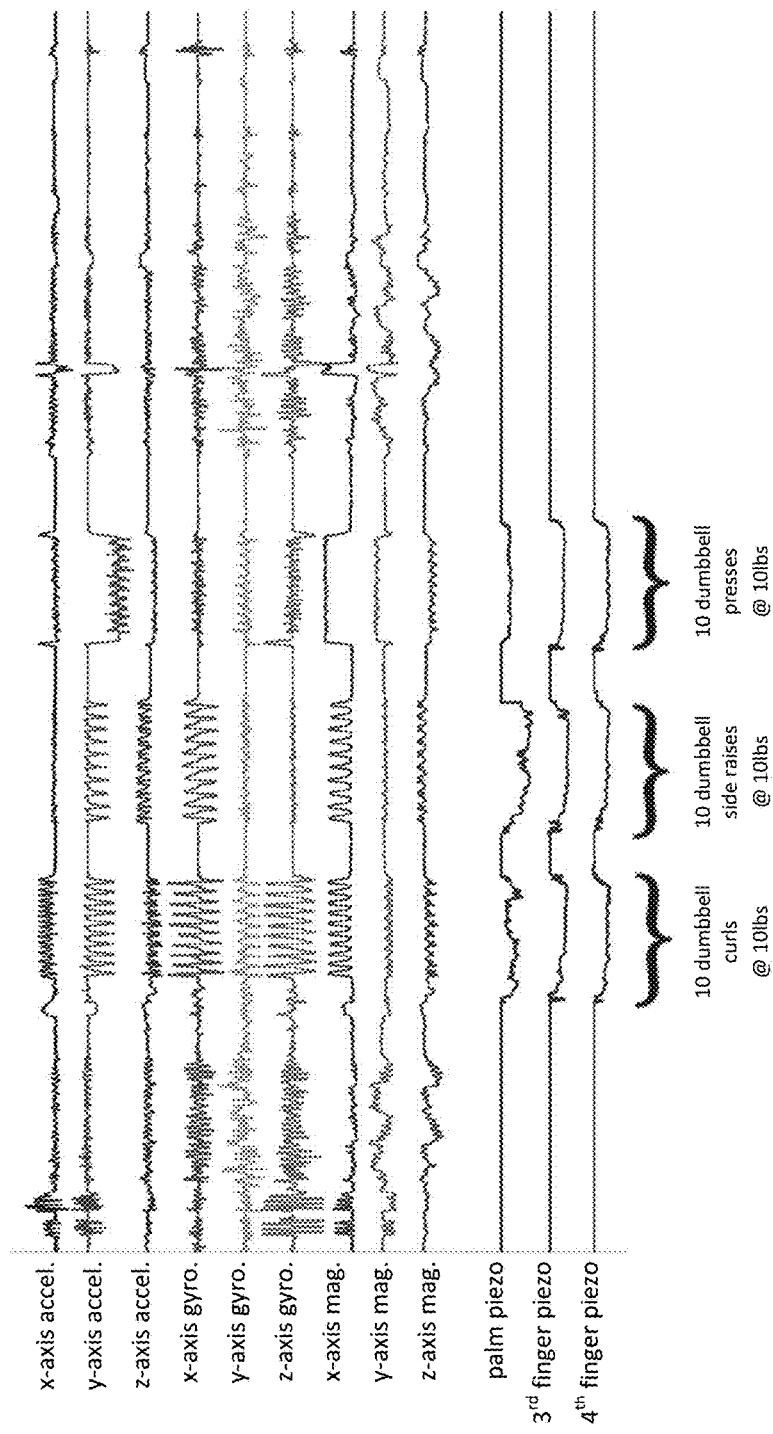
FIG. 13C is a plot of information received from the prototype weightlifting glove of FIGS. 13A, 13B.

FIGS. 13A-13C illustrate a version 2.3 of a prototype weightlifting glove 1300 according to an embodiment of the present disclosure. FIG. 13A illustrates prototype glove 1300 in a view from a back side of the hand when worn. In this prototype glove 1300, two fingers of the hand are fully covered by material, as shown by a third (middle) finger area 1305, and a fourth (ring) finger area 1310. The remaining fingers are partially covered in this embodiment. Third finger area 1305 and fourth finger area 1310 include sensors, as described below.

A prototype puck 1315 is shown placed within a receptacle 1320. A set of wires 1325 extend from puck 1315 to a connector 1330 on a programmable logic unit 1335 development board, which is a computing device 200. In this version of the prototype glove 1300, programmable logic unit 1335 is an Arduino Uno. A micro SD RAM memory is included with the Arduino Uno, and the Arduino Uno includes a Bluetooth™ protocol communication module.

Another set of wires 1340 extends from prototype glove 1300 to programmable logic unit 1335, as discussed below. A power source connector 1345 is attached to programmable logic unit 1335, as also discussed below.

In prototype glove 1300, programmable logic unit 1335 and a power source (discussed below) are mounted on the prototype glove 1300 for development. In a planned version, prototype puck 1315 will be replaced with a puck (e.g., 110) that includes a computing device and a power source (such as described with respect to FIG. 11).

FIG. 13B illustrates components of the prototype glove 1300 of FIG. 13A, including an outer glove portion 1301 and an inner glove portion 1302. Power source connector 1345 is attached to power source 1350.

Inner glove portion 1302 includes finger sensors 1355, positioned at the fingertips of third finger area 1305 and fourth finger area 1310. Inner glove portion 1302 further includes a palm sensor 1360. Finger sensors 1355 and palm sensor 1360 are piezoresistive fabric sensors in this prototype. As a weightlifting activity is performed, a pressure or change in pressure is detected from a measured resistance of the piezoresistive fabric. Conductors 1341 connect finger sensors 1355 and palm sensor 1360 through a connector 1342 to wires 1340.

As can be seen, prototype glove 1300 is an activity-specific article 130 (weight-lifting) lifting) in physical activity monitoring system 100. Activity-agnostic sensors are included in puck 1315. The activity-agnostic sensors of puck 1315 are in an inertial measurement unit (IMU) of an InvenSense MPU-9150. The IMU includes a 3-axis accelerometer, a 3-axis gyroscope, and a 3-axis magnetometer.

A subject wears prototype glove 1300 as shown in FIG. 13A, with inner glove portion 1302 against the skin, and outer glove portion 1301 over inner glove portion 1302. As the subject lifts a weight, the resistivity at finger sensors 1355 and palm sensor 1360 changes, and the resistivity or change in resistivity is measured by programmable logic unit 1335. Additionally, activity-agnostic acceleration, gyroscopic, and magnetometric information is acquired from the IMU. The information from the finger sensors 1355, palm sensor 1360 and IMU is stored in the micro SD memory and/or transmitted via Bluetooth to a computing device.

FIG. 13C is a plot of data received by programmable logic unit 1335 and transmitted to an external computing device via Bluetooth. Data of nine IMU signals are shown on the plot: accelerometer data in three axes (x, y, z), gyroscope data in three axes (x, y, z) and magnetometer data in three axis (x, y, z). Also plotted is resistivity from piezoresistive finger sensors 1355 and the palm sensor 1360. As indicated in FIG. 13C, the combination of information from the activity-specific finger sensors 1355 and the palm sensor 1360 with information from the IMU allows for a recognition of the specific activity that was performed. Specifically, a sequence of ten dumbbell curls, ten dumbbell side raises and ten dumbbell presses was performed. The combined information further provides for a determination that the activities were performed using a ten pound dumbbell.

When the weightlifting session is complete, puck 1315 may be removed from prototype glove 1300 and placed in a receptacle of another article 130, such as armband/wristband 1360.

Figure 14:
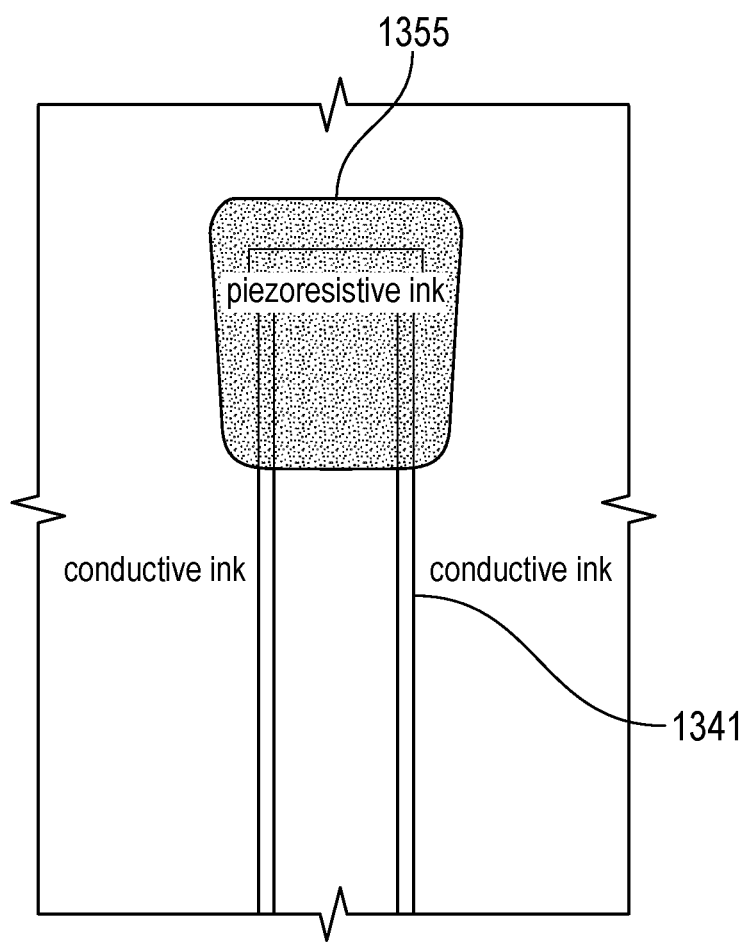
FIG. 14 illustrates an example of a piezoresistive sensor according to an embodiment of the present disclosure.

FIG. 14 illustrates one prototype finger sensor 1355 used in a version of prototype glove 1300. Finger sensor 1355 is a piezoresistive ink applied to a flexible fabric. Conductors 1341 are conductive ink applied to the flexible fabric. A dielectric material may be coated over one or both of the piezoresistive ink and the conductive ink, such as for electrical isolation or humidity protection. In other prototype versions, conductive thread or wire was applied to or woven into the material of the prototype gloves 1300 to form conductors 1341.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations is not a limitation of the disclosure.

What is claimed is:

1. A system, comprising:
   an activity-specific article, the article comprising:
   at least one receptacle; and
   at least one activity-specific sensor coupled to the receptacle; and
   at least one activity-agnostic puck configured to be removably positioned in the receptacle, the puck comprising:
   a processor;
   a communication interface; and
   at least one activity-agnostic sensor coupled to the processor;
   wherein the processor is configured to receive information from the activity-specific sensor and the activity-agnostic sensor, and provide the received information through the communication interface, and the processor is further configured to receive a unique identifier from the receptacle, and identify the receptacle or the activity-specific article from the unique identifier.

2. The system of claim 1, wherein the activity-specific article is a wearable clothing item.

3. The system of claim 1, wherein the processor is further configured to stamp the information from the activity-specific sensor with the unique identifier.

4. The system of claim 1, wherein the processor is further configured to stamp the information from the activity-agnostic sensor with a unique identifier of the activity-agnostic puck.

5. The system of claim 1, wherein the activity-specific sensor is a piezoresistive or piezoelectric sensor.

6. The system of claim 1, wherein the activity-specific sensor is a piezoresistive sensor formed of interspersed layers of a conductive material, a piezoresistive material, and an insulating material.

7. The system of claim 1, wherein the activity-agnostic sensor is an inertial measurement unit.

8. The system of claim 1, the puck further comprising a memory, wherein the processor is further configured to save the received information to the memory.

9. The system of claim 1, wherein the puck is waterproof.

10. A system, comprising:
    an activity-specific article, the article comprising:
    at least one receptacle; and
    at least one activity-specific sensor coupled to the receptacle, wherein the activity-specific sensor is a piezoresistive sensor formed of a piezoresistive ink; and
    at least one activity-agnostic puck configured to be removably positioned in the receptacle, the puck comprising:
    a processor;
    a communication interface; and
    at least one activity-agnostic sensor coupled to the processor;
    wherein the processor is configured to receive information from the activity-specific sensor and the activity-agnostic sensor, and provide the received information through the communication interface.

11. A method, comprising: while a puck is removably positioned in a first receptacle;
    collecting first activity-specific sensor information through the first receptacle during a first activity period; and
    transmitting second activity information from a memory of the puck through a communication interface of the puck;
    wherein the second activity information represents second activity-specific sensor information received by the puck through a second receptacle during a second activity period prior to the first activity period, and further represents activity-agnostic sensor information received from within the puck during the second activity period.

12. The method of claim 11, wherein the first or second activity-specific sensor information is pressure or force, or a combination thereof.

13. The method of claim 11, wherein the activity-agnostic sensor information is acceleration, velocity, orientation, or gravitational force, or a combination thereof.

14. The method of claim 11, further comprising transmitting third activity information from the memory of the puck through the communication interface of the puck, wherein the third activity information represents third activity-specific sensor information received by the puck through a receptacle of a third article during a third activity period prior to the second activity period.

15. A sealed removable puck, comprising:
a processor;
a communication interface coupled to the processor;
at least one sensor, the at least one sensor comprising an inertial measurement unit;
a sensor interface coupled to the sensor;
a physical interface configured for coupling to a receptacle;
wherein the processor is configured to:
 identify, through information received via the physical interface when coupled to the receptacle, an activity-specific article to which the receptacle is attached by receiving a unique identifier from the physical interface, wherein the processor is further configured to stamp the activity-specific sensor information with the unique identifier;
 receive activity-specific sensor information through the physical interface;
 receive activity-agnostic sensor information from the sensor interface; and
 provide the received activity-specific and activity-agnostic sensor information wirelessly through the communication interface.

16. The sealed removable puck of claim 15, wherein the at least one sensor includes a pulse rate sensor.

17. The sealed removable puck of claim 15, wherein the processor is further configured to stamp the activity-agnostic sensor information with a unique identifier of the puck.

* * * * *